(12) United States Patent
Torres Cardoso et al.

(10) Patent No.: US 12,138,194 B2
(45) Date of Patent: Nov. 12, 2024

(54) MEDICAL DEVICE FOR CONTROLLING THE RELEASE OF WASTE CONTENT FROM A SUBJECT, USES AND METHOD THEREOF

(71) Applicants: ASSOCIATION FOR THE ADVANCEMENT OF TISSUE ENGINEERING AND CELL BASED TECHNOLOGIES & THERAPIES A4TEC—ASSOCIAÇÃO, Braga (PT); TRIPLE IDEA LDA, Barcelos (PT)

(72) Inventors: Daniela Torres Cardoso, Barcelos (PT); André Manuel Macedo Santos, Barcelos (PT); André Torres Cardoso, Barcelos (PT)

(73) Assignees: ASSOCIATION FOR THE ADVANCEMENT OF TISSUE ENGINEERING AND CELL BASED TECHNOLOGIES & THERAPIES A4TEC—ASSOCIAÇÃO, Braga (PT); TRIPLE IDEA LDA, Barcelos (PT)

( * ) Notice: Subject to any disclaimer, the term of this patent is extended or adjusted under 35 U.S.C. 154(b) by 1043 days.

(21) Appl. No.: 17/046,201

(22) PCT Filed: Apr. 10, 2019

(86) PCT No.: PCT/IB2019/052966
§ 371 (c)(1),
(2) Date: Oct. 8, 2020

(87) PCT Pub. No.: WO2019/198012
PCT Pub. Date: Oct. 17, 2019

(65) Prior Publication Data
US 2021/0022909 A1    Jan. 28, 2021

(30) Foreign Application Priority Data

Apr. 10, 2018 (PT) .......................... 110676

(51) Int. Cl.
*A61F 5/441* (2006.01)
*A61F 5/44* (2006.01)
(Continued)

(52) U.S. Cl.
CPC ............ *A61F 5/441* (2013.01); *A61F 5/4401* (2013.01); *A61F 5/4407* (2013.01); *A61F 5/443* (2013.01);
(Continued)

(58) Field of Classification Search
CPC ........ A61F 5/44–449; A61F 2005/4415–4495; A61B 5/746; A61B 2562/0247
See application file for complete search history.

(56) References Cited

U.S. PATENT DOCUMENTS

| 4,232,672 A | 11/1980 | Steer et al. |
| 8,998,867 B2 | 4/2015 | Sabeti |

(Continued)

FOREIGN PATENT DOCUMENTS

| DE | 19953062 A1 | 5/2000 |
| EP | 0985390 A1 | 5/2000 |

(Continued)

*Primary Examiner* — Susan S Su
(74) *Attorney, Agent, or Firm* — Leason Ellis LLP

(57) ABSTRACT

The present disclosure relates to a compact medical device and method for controlling the release of waste content from an external stoma of a subject, comprising: a flange; wherein the flange comprises a vent hole and a vent cover for releasing gas waste content; an adhesive layer bound to the flange for attaching to the body of the subject; a displaceable cover for closing and opening the device, wherein the displaceable cover is configured to connect to the flange; an aperture configured to surround the stoma for the release of waste content.

17 Claims, 7 Drawing Sheets

(51) Int. Cl.
  *A61F 5/443*   (2006.01)
  *A61F 5/445*   (2006.01)
  *A61B 5/00*    (2006.01)
(52) U.S. Cl.
  CPC .............. *A61F 5/445* (2013.01); *A61B 5/746* (2013.01); *A61B 2562/0247* (2013.01)

(56) References Cited

U.S. PATENT DOCUMENTS

| | | |
|---|---|---|
| 2012/0109086 A1 | 5/2012 | Tsai |
| 2013/0060213 A1* | 3/2013 | Hanuka ................... A61F 5/441 604/344 |
| 2016/0166424 A1* | 6/2016 | Hanuka ................... A61F 5/441 604/335 |
| 2017/0140103 A1 | 5/2017 | Angelides |
| 2018/0333290 A1 | 11/2018 | Jones et al. |
| 2019/0133810 A1* | 5/2019 | Seres ....................... A61F 5/443 |

FOREIGN PATENT DOCUMENTS

| | | |
|---|---|---|
| EP | 2002811 A1 | 12/2008 |
| GB | 2431239 A | 4/2007 |
| WO | WO 1994015190 A1 | 7/1994 |
| WO | WO 2011/138727 A1 | 11/2011 |
| WO | WO 2012/058388 A1 | 5/2012 |
| WO | WO 2014102537 A1 | 7/2014 |

* cited by examiner

MEDICAL DEVICE FOR CONTROLLING THE RELEASE OF WASTE CONTENT FROM A SUBJECT, USES AND METHOD THEREOF

CROSS-REFERENCE TO RELATED APPLICATIONS

This application is a U.S. National Stage Application under 35 U.S.C. § 371 of International Patent Application No. PCT/IB2019/052966, filed Apr. 10, 2019, which claims priority to Portugal Patent Application No. 110676, filed Apr. 10, 2018, the contents of which are each hereby incorporated by reference in their respective entireties.

TECHNICAL FIELD

The present disclosure relates to a medical device for controlling the release of intestinal content in colostomized patients, destined to all the patients that, for some reason, have been submitted to colostomy.

BACKGROUND

Colostomy consists of a surgical procedure in which a cross section of the colon is performed, with the anal region being sutured and closed, while the other portion is anastomosed to the abdominal wall.

After surgery, is mandatory that the patient uses a colostomy bag for waste collection. According to the ostomy procedure, temporary or definitive, the patient is submitted to, they may have to use the colostomy bag temporarily or "ad eternum". Invariably, there are several personal, intimate, social and professional aspects that change during this process. A colostomized patient loses control over his/her body, namely flatulence and stool output, carrying innumerable physical and psychological problems and limitations, whose severity will depend on patient resilience.

Worldwide, the real prevalence of the problem is impressive. Just in the United States of America (USA) and according to the "United Ostomy Associations of America", there are over 750.000 Americans with at least one kind of ostoma—36.1% (270.000) with colostomy and 32.3% (242.000) with ileostomy. Also, in the USA, there are over 100.000 new ostomy surgeries, every single year.

In Portugal, the estimated number of ostomized patient is between 10.000 to 12.000, while in the European Union (UE) there are nearly 700.000 (RTP, 2015) (Eucomed-Medical Technology, 2012 a) (Eucomed-Medical Technology, 2012 b). The studies analyzed do not allow the precise indication of the number of colostomized patients in Portugal or internationally, but they provide an elucidative perspective over the relevance of this health problematic.

Waste collecting systems, are responsible for managing the main ostomies problem: waste collection. Therefore, there has been a great effort from manufacturers to improve some of the products features: gas filters, fixation system and some other small details. Nevertheless, only small changes have been performed, keeping the overall concept untouched. In a general way, there has been an incredible evolution in medical devices in the past few years, accompanying the technology available. Colostomy related devices, despite great scientific effort to try to come up with alternatives to colostomy bags, namely artificial sphincters and occluded systems, have not yet find a truly effective alternative until now.

The document U.S. Pat. No. 8,998,867B2 discloses an ostomy device configured with an implant arranged, in use, to be located inside the body of person near the site of a stoma. A discharge device is arranged, in use, to provide means for intestinal waste to exit to the exterior of the body of the person. In addition, there is means, in use, to be operatively associated with the implant and removably locate the discharge device at the site of the stoma. The discharge device is retained at the site of the stoma by magnetic attraction between the implant and the discharge device.

As mentioned in patent document U.S. Pat. No. 8,998, 867B2, this device aims to eliminate the ostomy bag. However, it is considerably more complex since it requires a surgery for the definitive implantation of the device inside the patient's body, which may cause several complications, namely implant rejection and discomfort. Up to the moment we have not yet found this product to be already marketed.

The document U.S. Pat. No. 2018/333290A1 relates to a reliably drain bodily waste from a reusable and drainable medical device such as an ostomy pouch.

The document WO201258388A1 relates to a controlled evacuation ostomy appliance comprising: a pouch having first and second walls, the first wall including a stomal aperture; a non-entrant stoma seal; an inner coupling member coupled to support the stoma seal for retaining the stoma seal in an operative position with respect to the stomal aperture; an outer coupling member around the inner coupling member for supporting the appliance; a cover of flexible impact-absorbing material covering at least a portion of the second wall opposite the stomal aperture, the cover comprising a retainer for retaining the lower portion of the pouch in the folded-up condition.

The document U.S. Pat. No. 2012/0109086A1 relates to a controlled discharge ostomy appliance, in particular with a stoma occluding seal.

These facts are disclosed in order to illustrate the technical problem addressed by the present disclosure.

General Description

The present disclosure relates to a medical device for controlling the release of intestinal content in colostomized patients, destined to all the patients that, for some reason, have been submitted to colostomy. The colostomy bag will no longer have to be visible, allowing the control over gas and feces release to the moment and the place the patient chooses it to be the most suitable, avoiding uncomfortable noises and smells.

Taking all into consideration and given the extent of the problem, affecting millions worldwide, we have decided to take a step forward, innovating the device for controlling the release of intestinal content, and creating the present disclosure, that we believe is going to considerably improve patient's quality of life and self-esteem.

This non-invasive device, besides allowing a significant life quality improvement to its user, also allows greater autonomy, freedom and intimacy preservation.

In an embodiment, this device is a long term device, reusable, totally washable, and/or use sterilizable product, represents an improvement comparing to other available products on the market.

An aspect, the present disclosure relates to a compact medical device for controlling the release of waste content from an external stoma of a subject, comprising: a flange; wherein the flange comprises a vent hole and a vent cover for releasing gas waste content; an adhesive layer bound to the flange for attaching to the body of the subject; a displaceable cover for closing and opening the device, wherein the displaceable cover is configured to connect to the flange; an aperture configured to surround the stoma for the release of waste content.

In an embodiment, said medical device comprises a pressure sensor for determining the pressure of the person waste content in the displaceable cover; an alert system; and data processor able to activate the alert system when the pressure is equal or superior to a pre-determined threshold.

In an embodiment, the pressure threshold is at least 120 mm Hg, preferably between 5-90 mm Hg, more preferably is at least 15-80 mm Hg, even more preferably is at least 20-60 mm Hg.

In an embodiment, said medical device further comprises a second flange, wherein the flanges are connectable/connected.

In an embodiment, the pressure threshold is regulable for fitting the subject feature.

In an embodiment, said medical device comprises a foldable container.

In an embodiment, the foldable container is attachable/attached to the second flange.

In an embodiment, said foldable container comprises a stoma contact face configured to be located on the stoma.

In an embodiment, said stoma contact face is concavely arranged for connecting on the stoma.

In an embodiment, said stoma contact face is a sponge, a gaze, a cotton, or combinations thereof, among others.

In an embodiment, the foldable container is a colostomy bag, an ileostomy bag, a urostomy bag, a trachea bag, or combinations thereof, among others.

In an embodiment, the colostomy bag is a compact colostomy bag, a compact ileostomy bag, a compact urostomy bag, a compact trachea bag, or combinations thereof.

In an embodiment, said medical device further comprising a temperature sensor, a gas sensor, or combinations thereof.

In an embodiment, the displaceable cover is vertically displaceable cover. In particular, the displaceable cover is removable.

In an embodiment, the displaceable cover is rotatably or magnetically attached to the first or the second flange.

In an embodiment, the adhesive layer is rotatably or magnetically attached the flange for fixing on the subject's body.

In an embodiment, the adhesive layer is attached with glue the flange for fixing on the subject's body.

In an embodiment, the flange is rotatably or magnetically coupled to at least one flange.

In an embodiment, the first flange is coupled with glue to the second flange.

In an embodiment, the foldable container is disposable and/or biodegradable.

In an embodiment, said the vent hole and the vent cover are arranged between in the flange such that the pressure of the waste content is relieved by the opening of the vent cover.

In an embodiment, the vent hole or vent cover comprise odor filters, or an elastomeric barrier, or combinations thereof.

In an embodiment, the elastomeric barrier is sealed.

In an embodiment, the alert system further comprises a power source for supplying power to the alert system, in particular said power source is a battery.

In an embodiment, the battery is charged by induction, or USB port, or using the subject movements to extract electrical charges, or using the subject thermal temperature to extract electrical charges or combinations thereof, among others.

In an embodiment, the alert system comprises an alarm.

In an embodiment, the alarm is a visual alarm, a vibratory alarm, a sonorous alarm, a smartphone alarm, a smartwatch alarm, a tablet alarm, or combinations thereof or among others.

In an embodiment, the device further comprises a wi-fi system, a Bluetooth system or combinations thereof or among others.

In an embodiment, the said medical device is watertight.

In an embodiment, the waste content is a body fluid, in particular intestinal content, more in particular solid, liquid or gaseous intestinal content.

In an embodiment all the components of the medical device is a suitable polymer.

Another aspect of the present disclosure relates to an ostomy pouch comprising the medical device described in any of the embodiments. In particular, the ostomy pouch is a colostomy pouch, an ileostomy pouch, an urostomy pouch, a trachea pouch, or combinations thereof.

Another aspect of the present disclosure relates to a method for controlling the release of waste content from an external stoma of a subject using the device of the present disclosure:

fixing the device of the present disclosure to the subject's body, determined the pressure of the subject intestinal content, using the data processor for processing the captured pressure of the person intestinal content for activating the alert system when the pressure is equal or superior to a pre-determined threshold. Preferably, the alert system may be deactivated by the subject.

BRIEF DESCRIPTION OF THE DRAWINGS

The following figures provide preferred embodiments for illustrating the description and should not be seen as limiting the scope of disclosure.

DETAILED DESCRIPTION

The present disclosure relates to a compact medical device and a method for controlling the release of waste content from an external stoma of a subject, comprising: a flange; wherein the flange comprises a vent hole and a vent cover for releasing gas waste content; an adhesive layer bound to the flange for attaching to the body of the subject; a displaceable cover for closing and opening the device, wherein the displaceable cover is configured to connect to the flange; an aperture configured to surround the stoma for the release of waste content.

The following figures provide preferred embodiments for illustrating the description and should not be seen as limiting the scope of disclosure.

Figure 1:
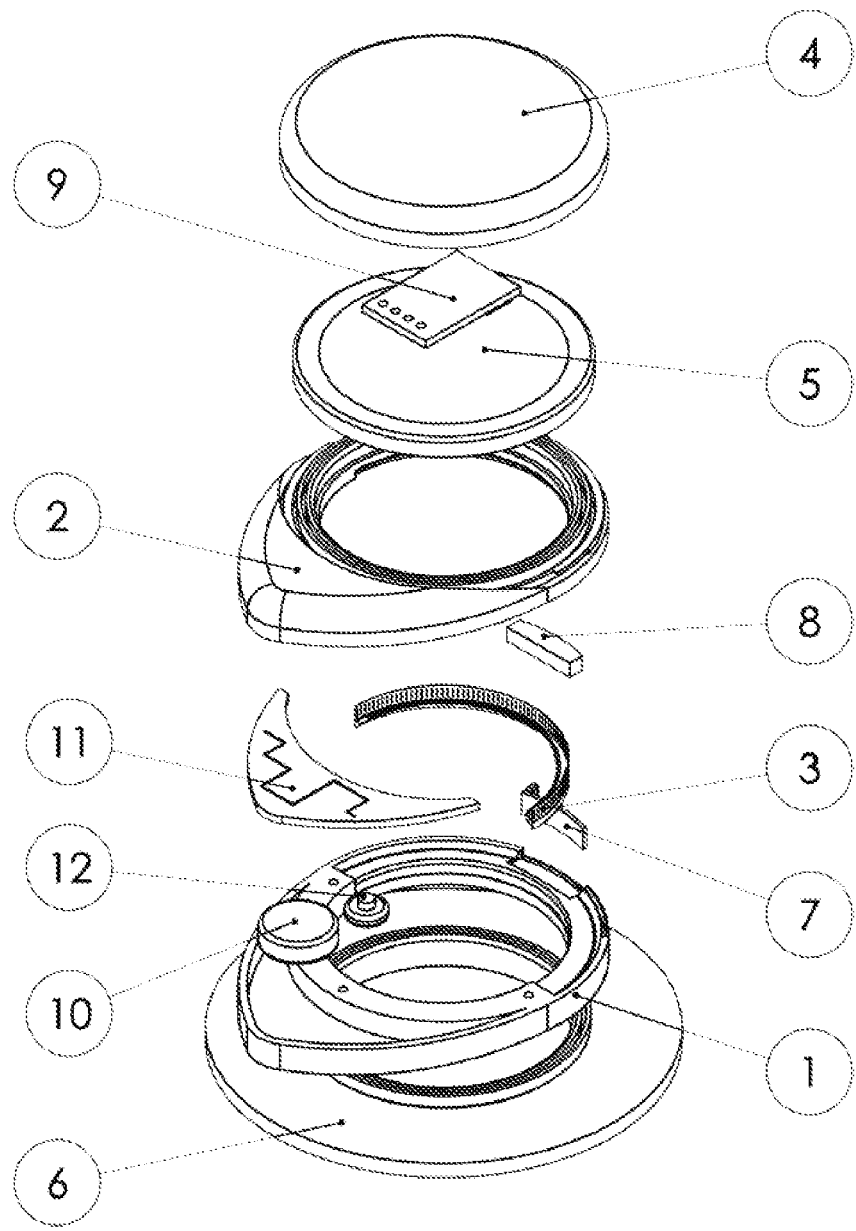
FIG. 1 shows a schematic representation of an embodiment of the complete medical device for controlling the release of intestinal content in colostomized patients.
Figure 2:
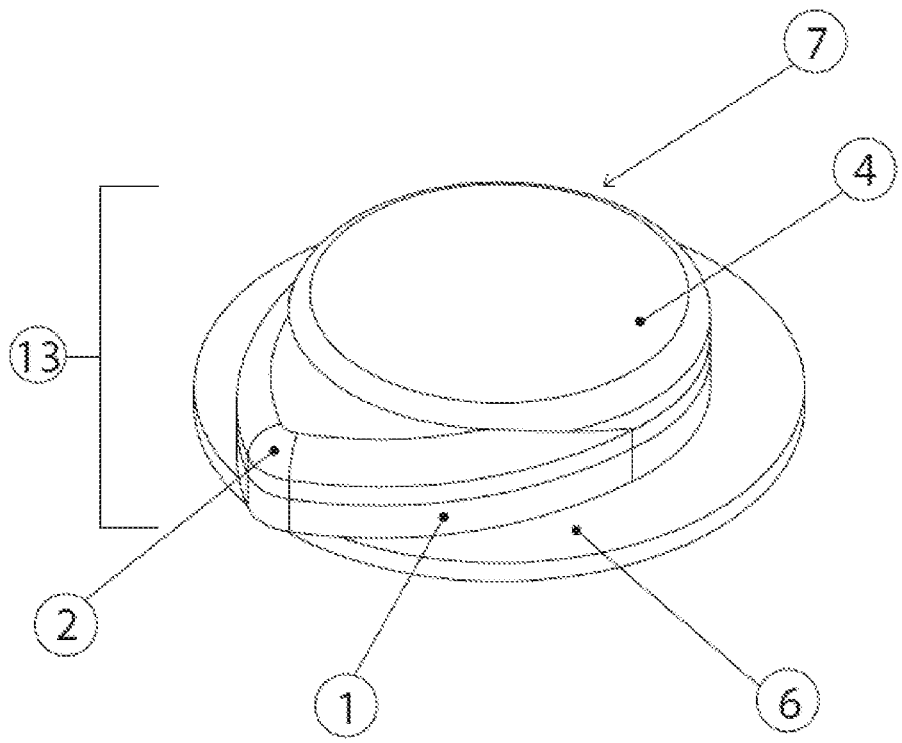
FIG. 2 shows a schematic representation of the perspective view of closed device placed on the user's body.
Figure 3:
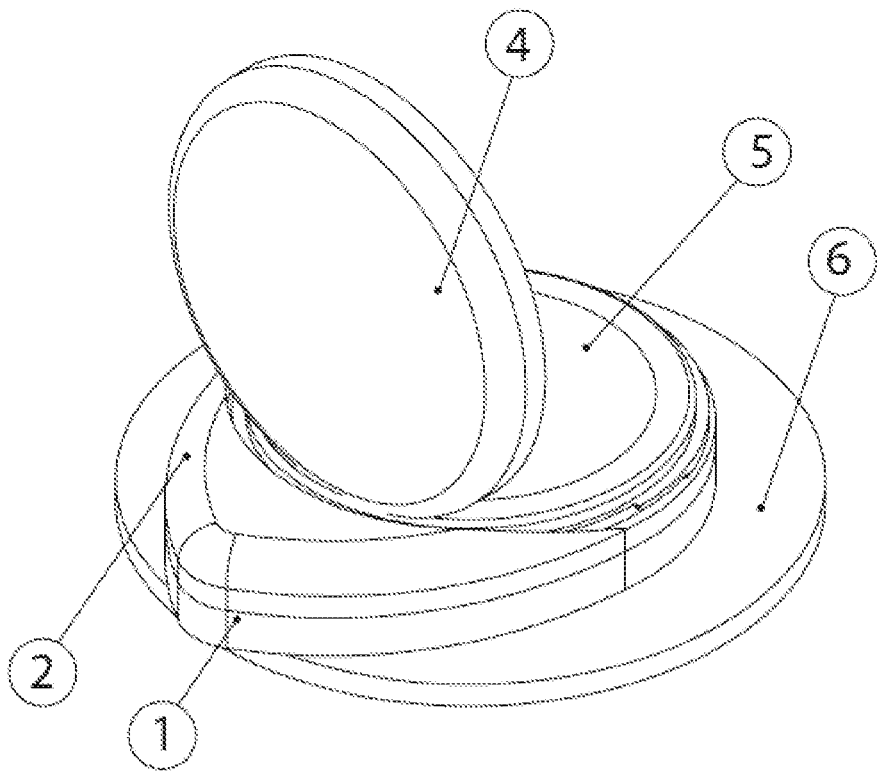
FIG. 3 shows a schematic representation of the perspective view of the device with the upper cover open and the compacted collection bag placed on the wearer's body.
Figure 4:
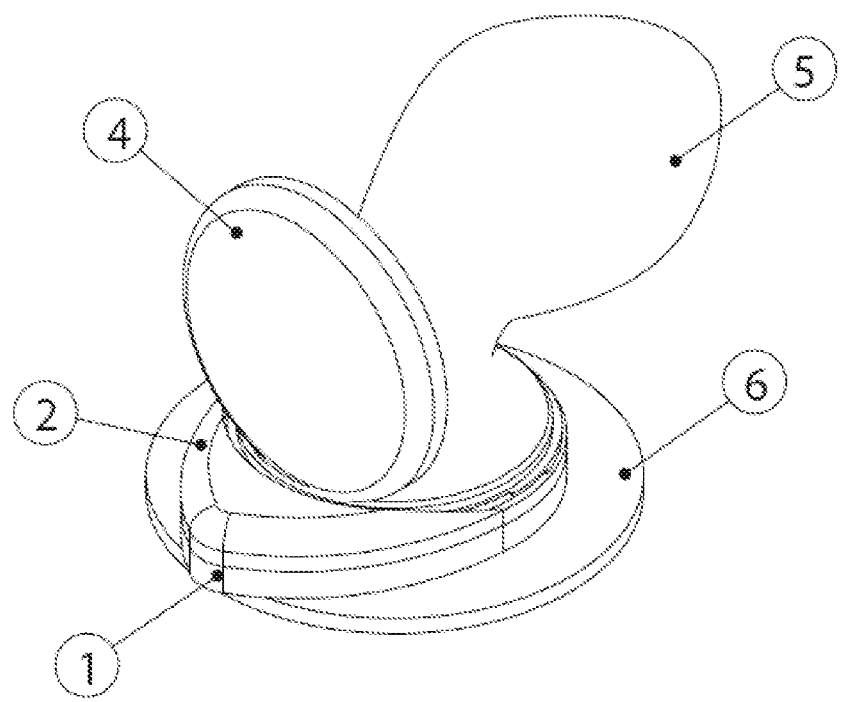
FIG. 4 shows a schematic representation of the perspective view of the device with the lid open and the expanded collection bag placed on the wearer's body.
Figure 5:
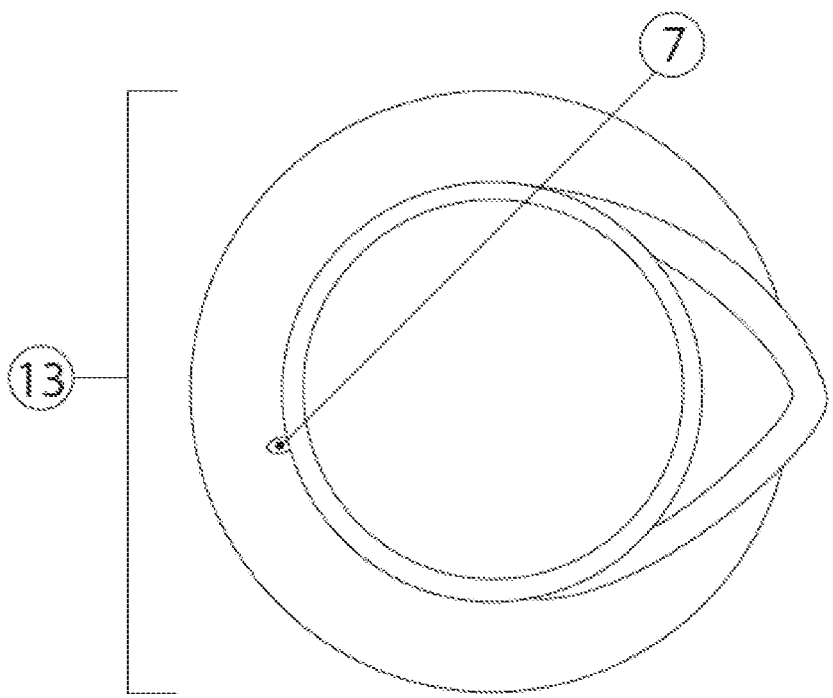
FIG. 5 shows a schematic representation of the front view showing of the complete device for controlling the release of intestinal content in colostomized patients.
Figure 6:
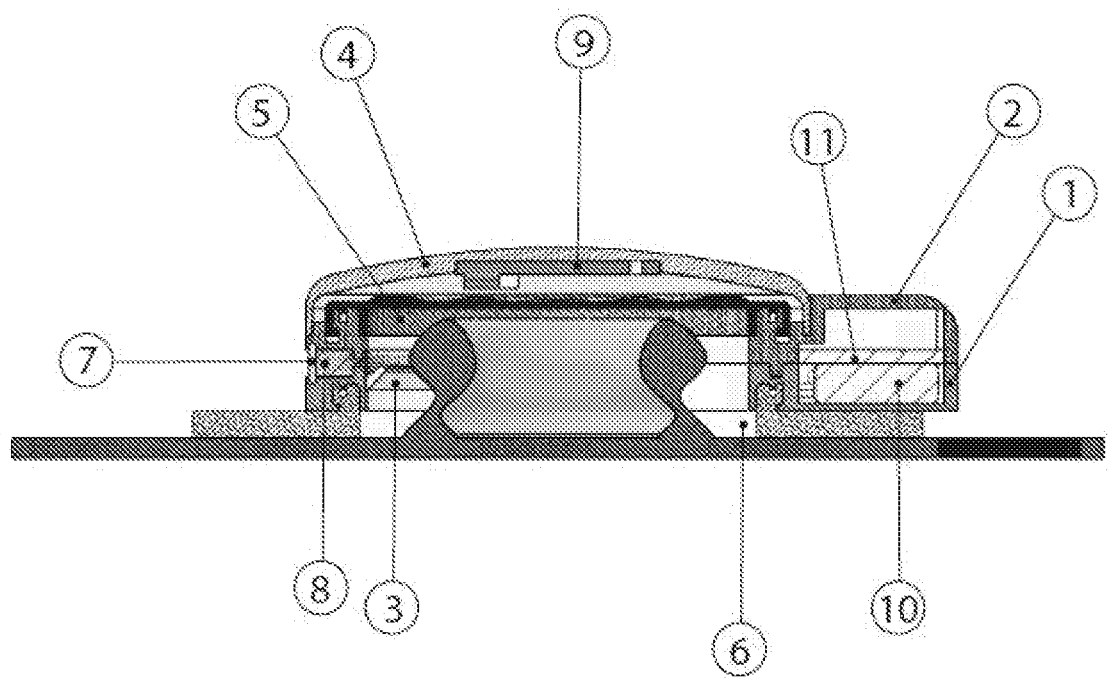
FIG. 6 shows a schematic representation of the device for controlling the release of intestinal content in colostomized patients (cross-section view).
Figure 7:
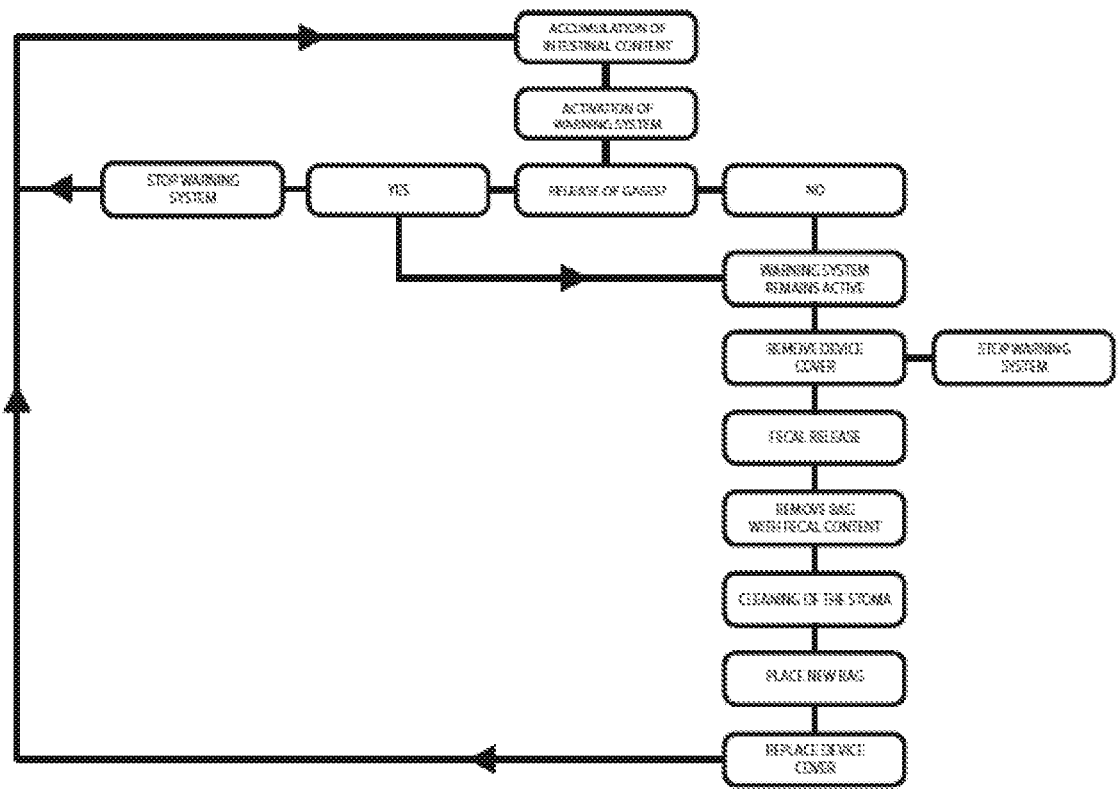
FIG. 7 shows a schematic representation about the method detailed operation.
Figure 8:
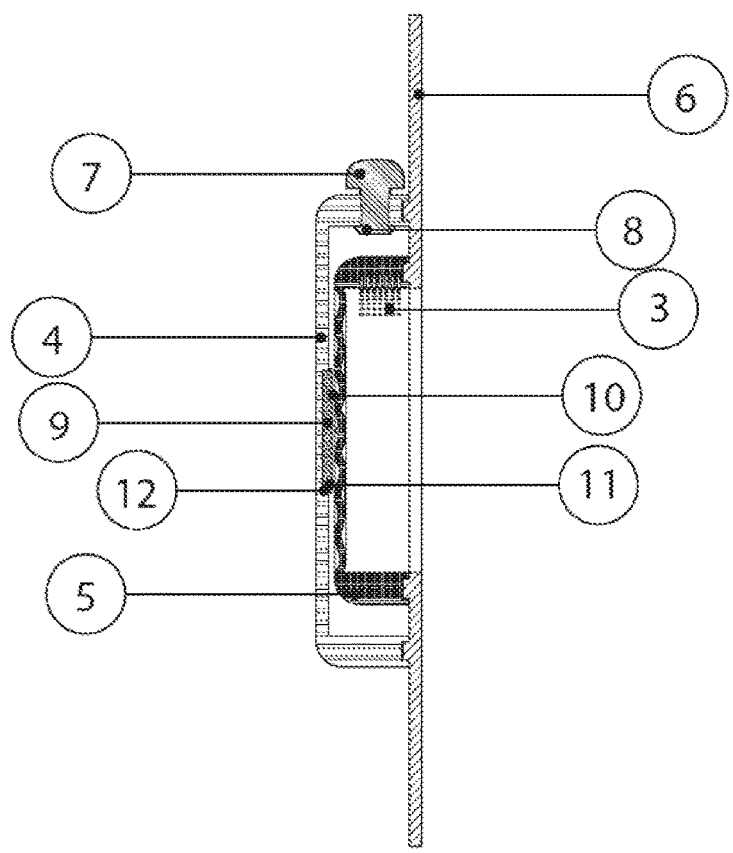
FIG. 8 shows a schematic representation of the lateral view of the device.
Figure 9:
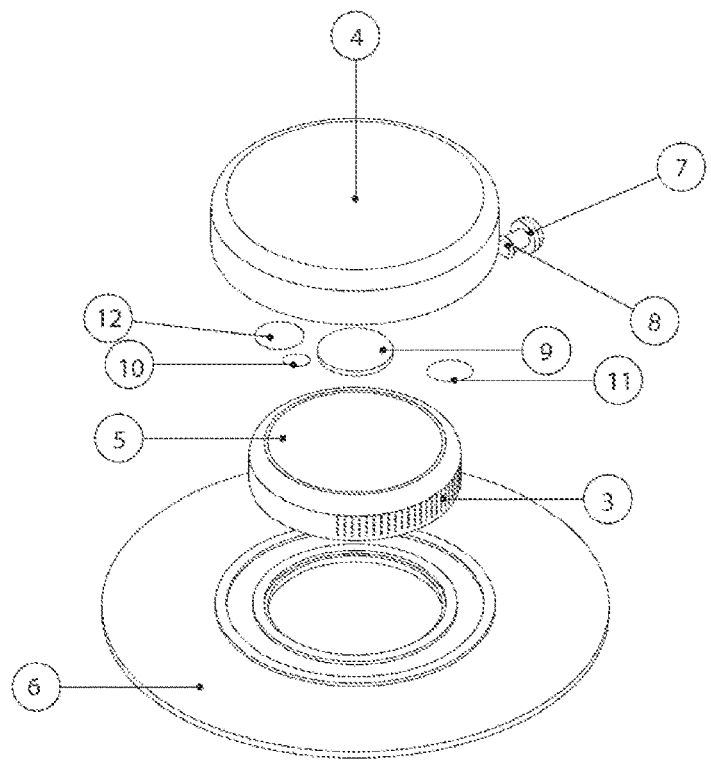
FIG. 9 shows a schematic representation of the main elements of the device with alternative form.
Figure 10:
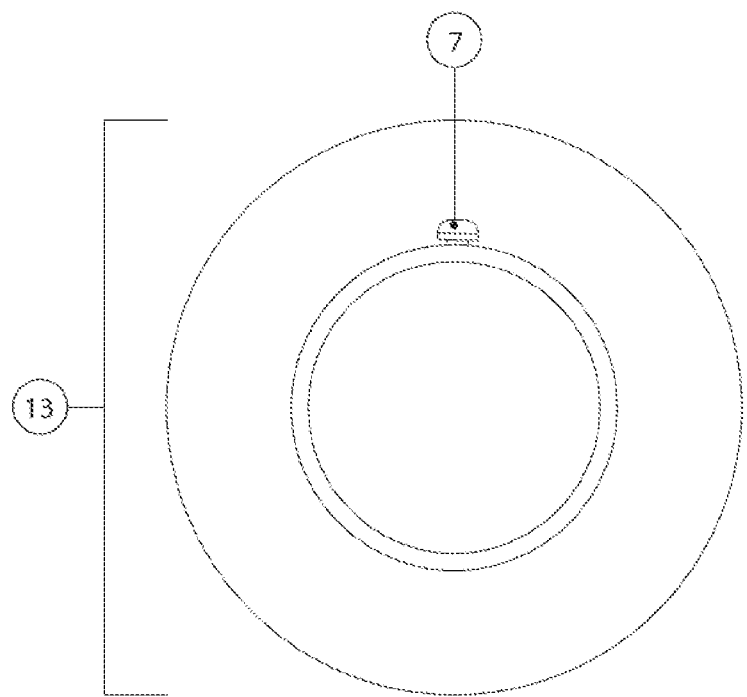
FIG. 10 shows a schematic representation of the top view of the device with alternative form.
Figure 11:
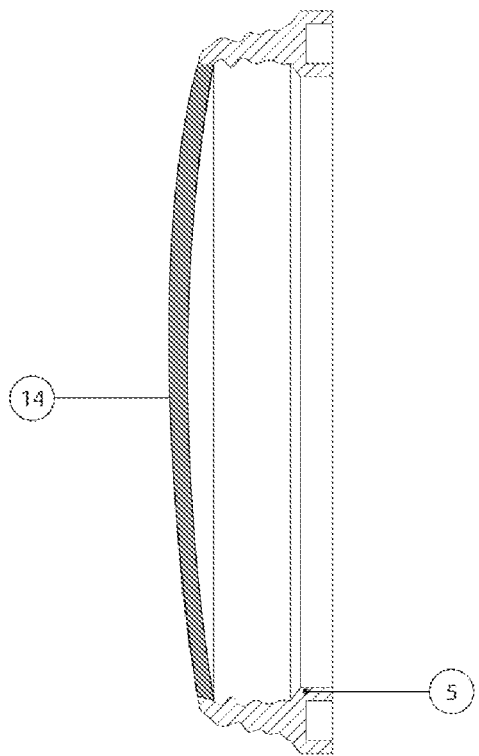
FIG. 11 shows a schematic representation of the perspective view of the device with alternative form.
Figure 12:
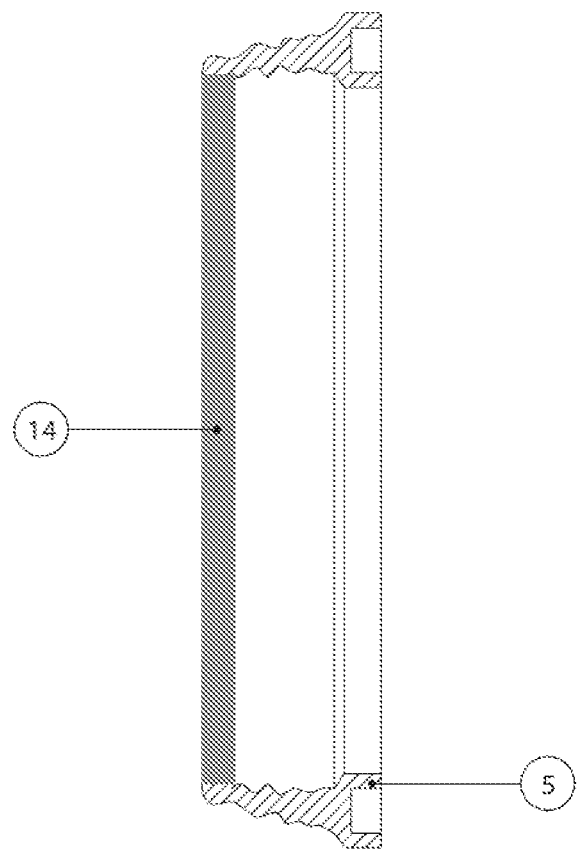
FIG. 12 shows a schematic representation of the perspective view of the device with alternative form.

In an embodiment, the device of the present disclosure is totally waterproof, washable and non-invasive. It is composed by an exterior component 13, with minimalist design, and a front opening through a displaceable cover 4. In an alternative embodiment, a cover 14 is provided and positioned above the colostomy bag 5 system (see FIGS. 11 and 12).

In an embodiment, the device of the present disclosure is fixed to the body through an adhesive layer 6, like the ones already existing in the market, therefore preventing the release of feces, gases and smells in an uncontrolled way. Its fixing point occurs over the abdominal wall and does not require any extra surgical intervention.

In an embodiment, inside the device of the present disclosure there is a disposable component 13, composed by a fully compacted colostomy bag 5, resembling an "airbag"-like system. Between this component and the ostoma, there is a vent cover 7, with odor neutralizer 8, for gas release control. Between the displaceable cover 4 and the colostomy bag 5 system, there is a pressure sensor 9. Once the intestinal content starts exerting pressure, predetermined to safe and adequate pressure values, the sensor 9 inside the device activates an electronic alert 12 (vibratory, sonorous or bright sign), synchronized with, for example, a smartphone app, that informs the patient about the need to go to an appropriate place for releasing the intestinal content.

In an embodiment, the relief of intestinal pressure, which may be due to feces or gases, can be distinguished in two different ways, depending on the reason for the sensor 9 activation:

In an embodiment, if there are gases inside the device 13, they are released through the activation of a vent cover 7;

In an embodiment, if there are feces inside the device, the user just has to open the displaceable cover 4 and automatically, due to pressure variation, the collection bag 5 inside the equipment, properly compacted, will expand and fill with fecal content. Once the release is over, the user removes the biodegradable bag component 5, does the sanitation and substitutes it for a new one.

In an embodiment, the device engages the fastening system by engagement and rotation against element 3, followed by a "click" ensuring the correct fixation of the piece. So that it does not inadvertently disengage, its unlock will have to be activated through a simultaneous manual pressure of one point and rotation of the entire piece (second flange 2 and first flange 1). When the predefined pressure of the intestinal content is reached, the pressure sensor 9 will activate the alert system 12 that will send a sign, vibratory, sonorous, bright and/or to a smartphone app, informing the user to the need of going to a proper place in order to empty the collection bag 5.

In an embodiment, the user will have to manually activate the vent valve to purge gases. This action will relieve the pressure therefore deactivating the alert system 12. If the alarm does not deactivate, the user will have to manually open the upper cover 4 and the pressure relieve will occur naturally, inflating the ostomy bag 5 in the device with intestinal content. Then, the user will remove de collecting bag 5 already full, do the sanitation and put a new bag 5, closing the displaceable cover 4.

In an embodiment, the device 13 is properly sealed so that the electrical and electronic systems 10, 11 and 12 will not be damaged while in use. The fast engagement systems (second flange 2 and first flange 1) in the device, besides user friendly are also watertight, to prevent any unpleasant surprises to the user.

In an embodiment, the electrical energy supply to the device comes from a battery 10, easily recharged by the user, through an access in the device 13.

In an embodiment, the disclosure is totally removable, washable and sterilizable, so that the user can clean it whenever necessary.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof. The above described embodiments are combinable. The following claims further set out particular embodiments of the disclosure.

The invention claimed is:

1. A medical device for controlling the release of waste content from an external stoma of a subject, comprising:
    a first flange;
    wherein the first flange comprises a vent hole and a vent cover for releasing gas waste content;
    an adhesive layer bound to the first flange for attaching to the body of the subject;
    a second flange, wherein the first and second flanges are connectable or connected;
    a displaceable cover for closing and opening the device, wherein the displaceable cover is configured to connect to the second flange;
    an aperture configured to surround the stoma for the release of waste content;
    an ostomy bag system;
    a pressure sensor for determining the pressure of the subject's waste content in the displaceable cover, wherein the pressure sensor is between the displaceable cover and the ostomy bag system;
    an alert system; and
    a data processor configured to activate the alert system when the pressure is equal or superior to a predetermined threshold.

2. The medical device according to claim 1, wherein the predetermined threshold is regulable.

3. The medical device according to claim 1, wherein said medical device comprises a foldable container and wherein said foldable container comprises a stoma contact face configured to be located on the stoma.

4. The medical device according to claim 3, wherein said stoma contact face is a sponge, a gauze, a cotton, a polymer or a combination thereof.

5. The medical device according to claim 1, further comprising a temperature sensor, a gas sensor, or a combination thereof.

6. The medical device according to claim 1, wherein the displaceable cover is rotatably or magnetically attached to at least the first flange.

7. The medical device according to claim 6, wherein the adhesive layer is rotatably or magnetically attached to at least the first flange for fixing on the subject's body.

8. A medical device according to claim 1, wherein the first flange is rotatably or magnetically coupled to the second flange.

9. The medical device according to claim 1, wherein the medical device comprises a foldable container which is made of a disposable and/or a biodegradable material.

10. The medical device according to claim 1, wherein said the vent hole and the vent cover are arranged between in the flange such that the pressure of the waste content is relieved by the opening of the vent cover.

11. The medical device according to claim 1, wherein the vent hole or vent cover comprise odours filters, or an elastomeric barrier, or a combination thereof.

12. The medical device according to claim 11, wherein the elastomeric barrier is sealed.

13. The medical device according to claim 1, wherein the alert system further comprises a power source for supplying power to the alert system.

14. The medical device according to claim 1, wherein the said medical device is watertight.

15. The medical device according to claim 1, wherein all the components of the medical device comprise a suitable polymer.

16. The medical device according to claim 1, wherein the ostomy bag system further comprises a colostomy pouch, an ileostomy pouch, an urostomy pouch, a trachea pouch, or a combination thereof.

17. A method for controlling the release of waste content from an external stoma of a subject using the device recited in claim 1, comprising:
    fixing the device recited in claim 1 on the subject's body,
    determining the pressure of the subject intestinal content, and
    using the data processor for processing the captured pressure of the person intestinal content for activating the alert system when the pressure is equal or superior to a pre-determined threshold.

* * * * *